United States Patent [19]

Eckhardt

[11] 4,309,436

[45] Jan. 5, 1982

[54] 3'(3,5-DICHLOROPHENYL)-SPIRO(3-OXABICYCLOC[3.1.0]HEXANE)-6,5'-OXAZOLIDINE-2',4'-DIONE

[75] Inventor: Wolfgang Eckhardt, Lörrach, Fed. Rep. of Germany

[73] Assignee: Ciba-Geigy Corporation, Ardsley, N.Y.

[21] Appl. No.: 161,985

[22] Filed: Jun. 23, 1980

[30] Foreign Application Priority Data

Jun. 27, 1979 [CH] Switzerland ........................ 5995/79
Jun. 3, 1980 [CH] Switzerland ........................ 4285/80

[51] Int. Cl.³ ..................... A61K 31/42; C07D 263/24
[52] U.S. Cl. ...................................... 424/272; 548/216
[58] Field of Search ........................ 548/216; 424/272

[56] References Cited

U.S. PATENT DOCUMENTS 4,200,643  4/1980  Knops et al. ...................... 548/216

FOREIGN PATENT DOCUMENTS 2852924  6/1980  Fed. Rep. of Germany ...... 548/216

Primary Examiner—Anton H. Sutto

Attorney, Agent, or Firm—Frederick H. Rabin

[57]  ABSTRACT

Compounds of the formula I

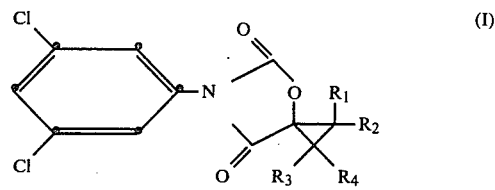

wherein at least one of the substituents $R_1$, $R_2$, $R_3$ and $R_4$ is $C_1$–$C_4$ alkyl and each of the others independently is hydrogen or $C_1$–$C_4$ alkyl, or, if $R_1$ and $R_3$ are both hydrogen, $R_2$ and $R_4$ can form a $C_2$–$C_4$ alkylene bridge in which one $CH_2$ member can be replaced by oxygen. These compounds possess valuable microbicidal properties, and they can be used in actual practice by themselves, or in the form of pesticidal compositions, especially for protecting cultivated plants from attack by fungus. The compounds of formula I have both a residual-protective and a systemic action.

3 Claims, No Drawings

3'(3,5-DICHLOROPHENYL)-SPIRO(3-OXABICY-CLOC[3.1.0]HEXANE)-6,5'-OXAZOLIDINE-2',4'-DIONE

The present invention relates to a compound of the formula I

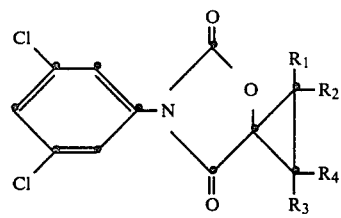
(I)

wherein at least one of the substituents $R_1$, $R_2$, $R_3$ and $R_4$ is $C_1$–$C_4$ alkyl and each of the others independently is hydrogen or $C_1$–$C_4$ alkyl, or, if $R_1$ and $R_3$ are both hydrogen, $R_2$ and $R_4$ can form a $C_2$–$C_4$ alkylene bridge in which one $CH_2$ member can also be replaced by oxygen.

Depending on the indicated number of carbon atoms, alkyl by itself or as moiety of another substituent denotes methyl, ethyl, propyl, butyl, isobutyl, sec-butyl, tert-butyl. A $C_2$–$C_4$ alkylene bridge is either an ethylene, propylene or butylene bridge.

The above exemplification does not entail any limitation.

The compounds of the formula 1 exist in the form of pairs of diastereoisomers. Their separation into the individual isomers can be accomplished in conventional manner, preferably with the educt III illustrated below or with the intermediate IV.

Unless otherwise indicated, throughout this specification the compounds of the formula I are mixtures of isomers. The compounds of the formula I possess microbicidal properties.

The compounds of the formula I can be obtained by numerous methods. In formulae II to XI, the substituents $R_1$ to $R_4$ are as defined for formula I, M is a metal cation, preferably an alkali metal cation, e.g. sodium or potassium, and R is alkyl.

Compounds of formula I can be obtained e.g. in accordance with one of the following schematic formulae A to E by reacting, in known manner, e.g. at room temperature, compounds of formula III, wherein R is hydrogen or alkyl, with isocyanates of formula II, and then cyclising the intermediates of formula IV, preferably at elevated temperature and optionally in the presence of a condensation agent, to give compounds of formula I:

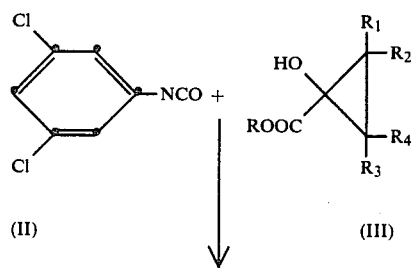

A.

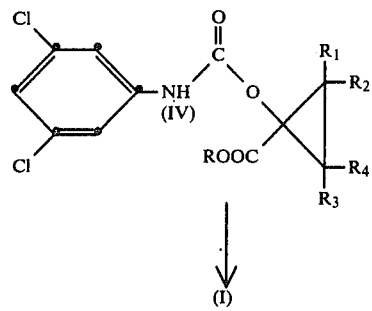

or by reacting compounds of formula V, preferably at room temperature, with isocyanates of formula II, and cyclising the intermediates, preferably at elevated temperature and optionally in the presence of an condensation agent, to give compounds of formula VIII, and converting these latter by acid hydrolysis into the end products of formula I:

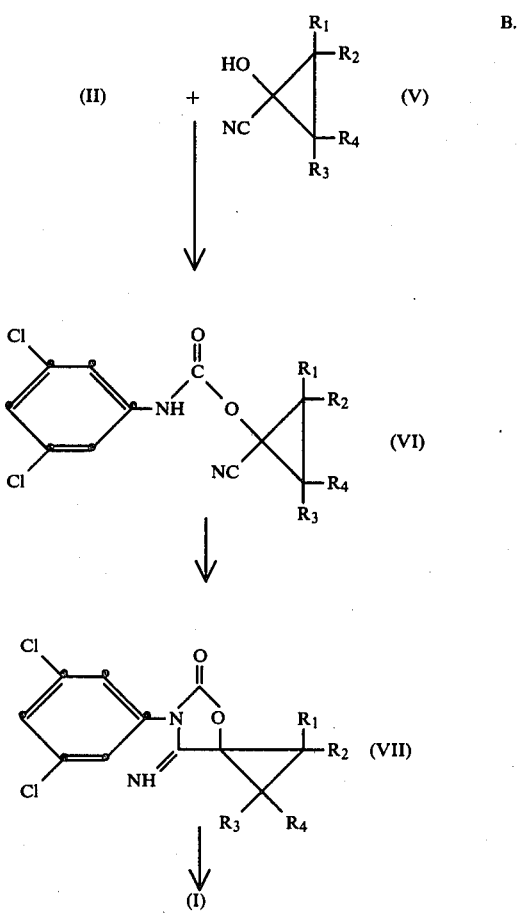

B.

or by condensing compounds of formulae III and IX with substituted anilines of formula VIII to give products of formula I:

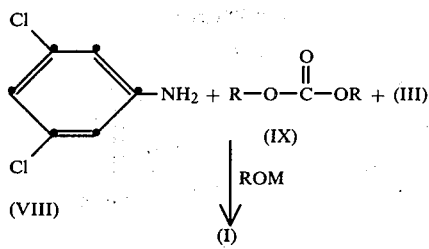

C.

or by reacting substituted anilines of formula VIII with compounds of formula X, preferably in the presence of an acid acceptor, to give intermediates of formula VI, and converting these latter, as described in process (B), into the final products of formula I:

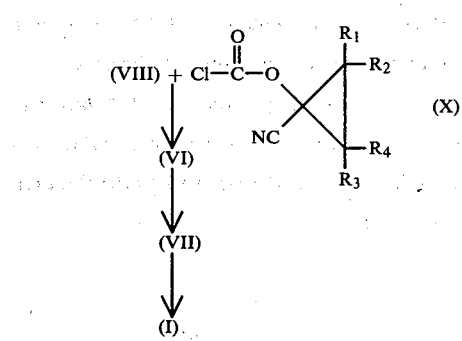

D.

or by condensing substituted anilines of formula VIII with compounds of formula XI, preferably in the presence of an acid acceptor, to give intermediates of formula IV, and converting these latter, as described in process (A), into the final products of formula I:

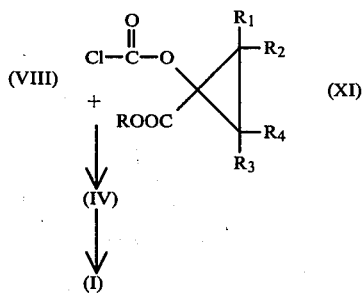

E.

In all the above processes, it is advantageous to conduct the reaction in a solvent which is inert to the reactants. The process can also be carried out in the absence of a solvent.

Examples of suitable solvents are: aromatic and aliphatic hydrocarbons such as benzene, toluene, xylenes, petroleum ether, ligroin, cyclohexane; halogenated hydrocarbons such as chlorobenzene, methylene chloride, ethylene chloride, chloroform, carbon tetrachloride, tetrachloroethylene; ethers and ethereal compounds such as diethyl ether, diisopropyl ether, tert-butyl methyl ether, dimethoxy ethane, dioxane, tetrahydrofurane, anisole; nitriles such as acetonitrile; ketones such as acetone, methyl ethyl ketone; esters such as ethyl acetate, butyl acetate; sulfones such as dimethyl sulfoxide; and mixtures of such solvents with the another.

In the above preparative methods, it is advantageous to neutralise liberated acids with appropriate acid acceptors. Examples of suitable acid acceptors are: organic bases such as trialkylamines (e.g. triethylamine), pyridine and pyridine bases, or organic bases such as oxides, hydroxides, bicarbonates, carbonates or hydrides of alkali metals or alkaline earth metals, as well as sodium acetate. In those cases where water is liberated, it is also possible to use, as condensation agent, carboxylic anhydrides such as acetic anhydride, or mineral acids such as hydrohalic acids, sulfuric acid, phosphoric acid or cyclohexylcarbodiimide. The acid acceptor or condensation agent is employed in at least equimolar amount, based on the amount of acid or water respectively that is liberated.

To hasten the cyclisation step in the preparative methods described above to give the corresponding 4-oxa-6-aza-spiro[2.4]heptane-5,7-diones, it is advantageous to carry out the process in the temperature range from $-10°$ to $160°$ C., preferably from $20°$ to $100°$ C. or at the boiling point of the solvent or solvent mixture.

The described processes can be carried out continuously and it is not absolutely necessary to isolate the intermediates of formulae IV, VI and VII.

The invention also relates to the various processes described above.

All starting materials are obtained by methods which are known per se. The compounds of formulae II, VIII and IX are known, whilst 1-hydroxy-cyclopropane-1-carboxylic acids of formula III are described in German Offenlegungsschrift No. 2 128 327 and can be converted in conventional manner into the derivatives of formulae V, X and XI (cf. also Liebigs Ann. Chemie, 1976, pp. 463–475). No biological properties of the starting materials have been reported. 3-(Phenyl)-oxazolidine derivatives are mentioned in J. Org. Chem. 32, No. 2, 383–88
Tetrahedron 26, No. 16, 3875–82 (1970)
Agr. Biol. Chem. 35, No. 11, 1707–19 (1971)

Surprisingly, it has been found that compounds having the structure of the formula I have, for practical purposes, a very much more advantageous microbicidal spectrum than the 3-(3′,5′-dichlorophenyl)-oxazolidine-2,4-diones of German Offenlegungsschrift No. 1 811 843.

Examples of cultivated plants within the scope of the present invention are: cereals, maize, rice, vegetables, soybeans, ground nuts, beans, fruit trees, berries, ornamentals, and in particular vines, hops, cucumber plants (e.g. cucumber, marrows, melons), solanaceae such as potatoes, tobacco and tomatoes, as well as bananas, cocoa and natural rubber plants.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

The content of active ingredient in commercial formulations is between 0.1 and 90% by weight.

For application the compounds of the formula I may be processed to the following formulations (in which the percentages refer to advantageous amounts of active ingredient):

Solid formulations:
  dusts, tracking agents (up to 10%), granules (coated granules, impregnated granules and homogeneous granules); pellets (1 to 80%);

Liquid formulations:
(a) active ingredient concentrates which are dispersible in water: wettable powders, pastes (25–90% in commercial packs, 0.01 to 15% in ready-for-use solutions); concentrated emulsions and solutions (10 to 50%; 0.01 to 15% in ready-for-use solutions);
(b) Solutions (0.1 to 20%); aerosols.

Such compositions likewise fall within the scope of this invention.

With the compounds of the formula I it is possible to inhibit or destroy the microorganisms which infect plants or parts of plants (fruit, blossoms, leaves, stems, tubers, roots) of these or related crops of useful plants, while parts of plants which grow later are protected against infection by such fungi and mites. The compounds of formula I are active against the phytopathogenic fungi belonging to the following classes: Fungi imperfecti (e.g. Botrytis), Ascomycetes such as Erysiphe, rust fungi such as Puccinia and Rhizoctonia pathogens.

The compounds of formula I furthermore have a systemic action and can also be used for protecting seeds (fruit, tubers and grains) and seedlings from attack by fungus infections as well as against microorganisms which occur in the oil.

Accordingly, the invention also relates to the use of compounds of formula I for controlling phytopathogenic microorganisms.

Preferred compounds within the scope of the formula I are those in which $R_1$ to $R_4$ are hydrogen or methyl. The most preferred compounds are compounds 1, 2, 3 and 15 specified below.

The following Examples will serve to illustrate the invention in more detail, but imply no limitation to what is described therein. Pressures are in millibars and parts are by weight.

EXAMPLE 1

(a) Preparation of the intermediate

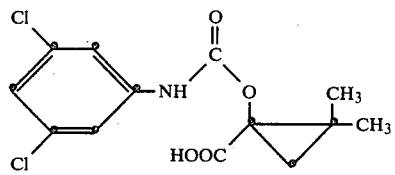

1-[N-(3',5'-dichlorophenyl)-carbonyloxy]-1-[(1,1-dimethyl)-cyclopropanecarboxylic acid 94 g (0.5 mole) of 3,5-dichlorophenylisocyanate are dissolved in 500 ml of toluene and 65 g (0.5 mole) of 1-hydroxy-1-(2,2-dimethyl)-cyclopropanecarboxylic acid are added at room temperature to this solution. The mixture is then stirred for 16 hours at room temperature and subsequently filtered. The filter cake is dried, affording 144 g of product with a melting point of 175°–176° C.

(b) Preparation of the final product

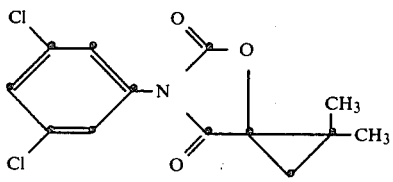

4-oxa-6(3',5'-dichlorophenyl)-1,1-dimethyl-spiro[2.4]-heptane-5,7-dione 20 g (0.063 mole) of 1-[N-(3',5'-dichlorophenyl)-carbonyloxy]-1-[(2,2)-dimethyl]-cyclopropanecarboxylic acid are stirred for 3 hours at 100° C. in 200 ml of acetic anhydride. After it has been cooled, the reaction mixture is poured into about 3 liters of ice-water and the precipitated product is collected by filtration, washed well with water and dried, affording 18 g of compound 2 with a melting point of 94°–96° C.

EXAMPLE 2

(a) Preparation of the intermediate

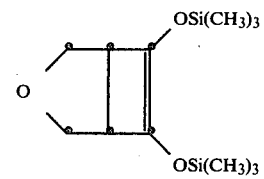

47.7 g (2.07 moles) of sodium are pulverised in 450 ml of toluene. A mixture of 106 g (0.49 mole) of tetrahydrofurane-3,4-dicarboxylic acid diethyl ester and 237 g (2.19 mole) of trimethylchlorosilane is then slowly added dropwise at 100° C. and the mixture is stirred for 16 hours at 100° C. bath temperature. After cooling, the mixture is filtered and the filtrate is concentrated. Distillation of the residue yields 54.2 g of product with a melting point of 109°–117° C./29 mbar.

(b) Preparation of the intermediate

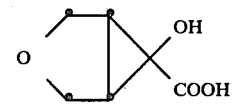

A solution of 32 g (0.2 mole) of bromine in 50 ml of pentane is slowly added dropwise at −40° C. in the course of 30 minutes to a solution of 54.4 g (0.2 mole) of the intermediate obtained in (a) in 50 ml of pentane. The reaction mixture is then poured into about 500 ml of 5% sodium hydroxide solution and stirred for 2 hours. The organic phase is separated and the aqueous solution is saturated with sodium chloride and then extracted with ether. The etheral solution is dried over sodium sulfate, filtered and concentrated. The residue is triturated with a small amount of ether, filtered and dried, affording 13.3 g of product with a melting point of 135°–137° C.

(c) Preparation of the intermediate

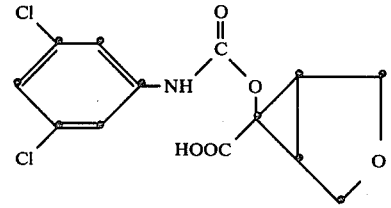

A solution of 9.4 g (0.05 mole) of 3,5-dichlorophenylisocyanate in 60 ml of toluene is added dropwise at room temperature to a solution of 7.2 g (0.05 mole) of the intermediate obtained in (b) in 60 ml of ether. The reaction mixture is then stirred for 1 day at room temperature and then filtered. The residue is triturated with ether, filtered and dried, affording 8.8 g of product.

(d) Preparation of the final product

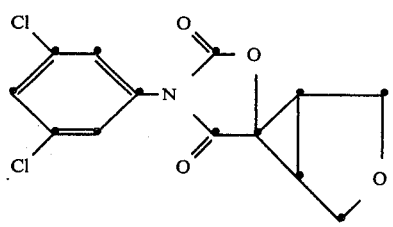

(compound 15)

8.8 g (0.026 mole) of the intermediate obtained in (c) are stirred for 3 hours at 100° C. in 100 ml of acetic anhydride. The mixture is cooled and concentrated. The residue is triturated with water, filtered and dried, affording 4.2 g of product with a melting point of 191°–192° C.

The following compounds of the formula I can be prepared in analogous manner or by one of the methods described herein:

TABLE 1

| Compound | $R_1$ | $R_2$ | $R_3$ | $R_4$ | Physical data |
|---|---|---|---|---|---|
| 1 | $CH_3$ | H | H | H | m.p. 122–124° C. |
| 2 | $CH_3$ | $CH_3$ | H | H | m.p. 94–96° C. |
| 3 | $CH_3$ | H | $CH_3$ | H | m.p. 90–91° C. |
| 4 | $CH_3$ | $C_2H_5$ | H | H | m.p. 89–91° C. |
| 5 | $CH_3$ | $CH_3$ | $CH_3$ | $CH_3$ | m.p. 128–132° C. |
| 6 | $C_3H_7(n)$ | H | H | H | m.p. 124–126° C. |
| 7 | $C_3H_7(i)$ | H | H | H | m.p. 117–121° C. |
| 8 | $C_4H_9(n)$ | H | H | H | viscous |
| 9 | $C_4H_9(t)$ | H | H | H | m.p. 111–113° C. |
| 10 | $CH_3$ | $CH_3$ | $CH_3$ | H | viscous |
| 11 | $C_2H_5$ | H | H | H | m.p. 121–124° C. |

TABLE 2

($R_1$ and $R_3$ = H)

| Compound | A | Physical data |
|---|---|---|
| 12 | $-(CH_2)_4-$ | viscous oil |
| 13 | $-(CH_2)_3-$ | oil |
| 14 | $-(CH_2)_2-$ | oil |
| 15 | $-CH_2-O-CH_2-$ | m.p. 191–192° C. |

FORMULATION EXAMPLES

EXAMPLE 2

Dusts: The following substances are used to formulate (a) 5% and (b) a 2% dust:

(a)

5 parts of compound 3
95 parts of talcum;

(b)

2 parts of compound 15
1 part of highly dispersed silicic acid
97 parts of talcum.

The active ingredients are mixed with the carriers and ground and in this form can be processed to dusts for application.

EXAMPLE 3

Granulate: The following substances are used to formulate a 5% granulate:

5 parts of one of compounds 1 to 15
0.25 part of epoxidised vegetable oil
0.25 part of cetyl polyglycol ether
3.50 parts of polyethylene glycol
91 parts of kaolin (particle size 0.3–0.8 mm).

The active ingredient is mixed with epoxidised vegetable oil and the mixture is dissolved in 6 parts of acetone. Then polyethylene glycol and cetyl polyglycol ether are added. The resultant solution is sprayed on kaolin and the acetone is evaporated in vacuo. A microgranulate of this kind is advantageously used for controlling soil fungi.

EXAMPLE 4

Wettable powders: The following constituents are used to formulate (a) a 70%, (b) a 40%, (c) and (d) a 25% and (e) a 10% wettable powder:

(a)

70 parts of compound 3
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk (b)

40 parts of compound 15
5 parts of sodium ligninsulfonate
1 part of sodium dibutylnaphthalenesulfonic acid
54 parts of silicic acid (c)

25 parts of compound 2
4.5 parts of calcium ligninsulfate
1.9 parts of Champagne chalk/hydroxyethyl cellulose mixture (1:1)
1.5 parts of sodium dibutylnaphthalenesulfonate
10.5 parts of silicic acid
19.5 parts of Champagne chalk
28.1 parts of kaolin (d)

25 parts of compound 3
2.5 parts of isooctylphenoxy polyethylene ethanol
1.7 parts of Champagne chalk/hydroxyethyl cellulose mixture (1:1)
8.3 parts of sodium aluminium silicate
16.5 parts of kieselguhr
46 parts of kaolin (e)

10 parts of compound 15
3 parts of a mixture of the sodium salts of saturated fatty alcohol sulfates 5 parts of naphthalenesulfonic acid/formaldehyde condensate
82 parts of kaolin.

The active ingredients are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for leaf application.

EXAMPLE 5

Emulsifiable concentrate: The following substances are used to formulate a 25% emulsifiable concentrate:

25 parts of one of compounds 1 to 15
2.5 parts of epoxidised vegetable oil
10 parts of an alkylarylsulfonate/fatty alcohol polyglycol ether mixture
5 parts of dimethyl formamide
57.5 parts of xylene.

By diluting such a concentrate with water it is possible to prepare emulsions of the desired concentration which are especially suitable for leaf application.

BIOLOGICAL EXAMPLES

EXAMPLE 6

Action against Botrytis cinerea on beans (a) Residual protective action
Bean plants about 10 cm in height are sprayed with a spray mixture (0.02% of active ingredient) prepared from the active ingredient formulated as wettable powder. After 48 hours, the treated plants are infected with a conidia suspension of the fungus. The infected plants are incubated for 2 to 3 days at 95-100% relative humidity and 21° C., and evaluation of the fungus attack is then made.

(b) Systemic action
Bean plants about 10 cm in height are treated with a spray mixture (0.006% of active ingredient, based on the volume of the soil) prepared from the active ingredient formulated as wettable powder. Care is taken that the spray mixture does not come in contact with the parts of the plants above the soil. The treated plants are infected 48 hours later with a conidia suspension of the fungus. Evaluation of fungus attack is made after the infected plants have been incubated for 2-3 days at 95-100% relative humidity and 21° C.

In test (a), fungus attack is completely prevented with compounds 1 to 15. In test (b), fungus attack is prevented with compounds 1, 2, 3 and 15.

EXAMPLE 7

Action against Rhizoctonia solani in cotton plants (a) Action after soil application
The fungus is cultivated on sterile oat grains and added to a mixture of earth and sand. Dishes are then filled with the infected soil and sown with cotton seeds. Immediately after sowing, the test preparation formulated as wettable powder is poured over the soil in the form of an aqueous suspension (20 ppm of active ingredient, based on the volume of the soil). The dishes are then kept for 2-3 weeks at about 24° C. in a greenhouse and the soil is kept uniformly moist by gently spraying it with water. The emergence of the cotton plants is determined when evaluating the tests. Emergence of more than 90% of the plants is achieved with compounds 3 and 15. This result corresponds to the control test with non-infected soil.

EXAMPLE 9

Residual protective action against Erysiphe graminis on barley

Barley plants about 8 cm in height are sprayed with a spray mixture (0.02% of active ingredient) prepared from the active ingredient formulated as a wettable powder. The treated plants are dusted with conidia of the fungus after 3-4 hours. The infected barley plants are then stood in a greenhouse at about 22° C. The extent of the fungus infection is evaluated after 10 days. In comparison with control plants, fungus attack is completely inhibited after treatment with compounds 4 and 15.

What is claimed is:
1. The compound of the formula

[Chemical structure: 2,4-dichlorophenyl group attached to N, which is bonded to two C=O groups forming a ring with a dioxolane moiety]

2. A method of controlling and preventing attck by phytopathogenic microorganisms at a locus, which comprises applying to said locus a microbicidally effective amount of the compound according to claim 1.

3. A microbicidal composition containing as active ingredient a microbicidally effective amount of the compound according to claim 1, together with at least one suitable carrier and/or surface-active agent.

* * * * *